United States Patent [19]

Vadasz

[11] Patent Number: 4,457,752
[45] Date of Patent: Jul. 3, 1984

[54] SURGICALLY IMPLANTABLE PUMP

[76] Inventor: Csaba Vadasz, Richard-Wagner-Strasse 5, D-4930 Detmold, Fed. Rep. of Germany

[21] Appl. No.: 417,230

[22] Filed: Sep. 13, 1982

[51] Int. Cl.³ ............................ A61M 5/00; A61M 5/20
[52] U.S. Cl. ..................................... 604/135; 604/209; 604/153; 604/214; 604/891
[58] Field of Search ................... 604/65, 67, 135, 138, 604/131, 153, 154, 209, 210, 216, 224, 890, 891; 128/1 R, 1.3

[56] References Cited

U.S. PATENT DOCUMENTS 2,221,739  11/1940  Reiter ................................. 604/210
3,315,660   4/1967  Abella ................................ 128/769
3,923,060  12/1975  Ellinwood, Jr. ................. 604/891

Primary Examiner—Stephen C. Pellegrino
Attorney, Agent, or Firm—Eliot S. Gerber

[57] ABSTRACT

An internally powered pump is surgically implanted to eject liquid under control of the experimenter. The pump reservoir is flexible and contains the liquid to be ejected. The reservoir is collapsed by a piston which is pushed by a compressed spring. The spring is released, step-by-step, by a pawl and ratchet mechanism. The pawl is magnetically responsive and pivots when a magnetic field is applied to the pump.

10 Claims, 3 Drawing Figures

SURGICALLY IMPLANTABLE PUMP

BACKGROUND OF THE INVENTION

The present invention relates to surgical devices and more particularly to pumps for surgical implantation in living animals.

At the present time it is known that a pump may be made small enough to be surgically implanted in a laboratory animal. The pump may be filled with a liquid drug or other bioactive liquid. The pump, over a predetermined period of time, expels the liquid from its reservoir into the area into which it has been implanted, for example, the bloodstream or cerebrospinal fluid, or the liquid may be pumped to another area using a tubular catheter.

One such implantable pump is an osmotic pump which may be used for the delivery of drugs at a controlled rate. This osmotic pump is described in the following article: Theeuwes, F. and Yum, S. I. (1976), "Principles of the design and operation of generic osmotic pumps for the delivery of semisolid or liquid formulations", *Ann. Biomed. Eng.* 4(4), pages 343–353.

Another type of implantable pump is shown in U.S. Pat. No. 3,894,538 entitled "Device For Supplying Medicines", issued July 15, 1975, in which, in one embodiment, gas is slowly produced in one chamber of the pump to force the liquid from a collapsible reservoir. As with the osmotic pump, the rate of discharge of the liquid may not be changed by the experimenter after the device is implanted.

Although implantable pumps have received widespread utilization, they are subject to a number of limitations. In osmotic pumps the rate at which the pump expels its liquid is determined by the osmotic pressure of the fluid surrounding the pump. Since such osmotic pressure is relatively constant, the rate is also relatively constant. While a constant feed rate of liquid is desirable in many applications, in certain other applications and experiments it would be desirable to have the rate both variable and controllable by the experimenter. For example, the osmotic pump may effectively expel its liquid at a constant rate for a one-week or two-week period. There have been indications that longer life pumps may be available which would extend the life to over a month. However, if the rate of pumping of the liquid were under the control of the experimenter, then the liquid may be pumped infrequently, for example, once a week or even once a month, and the supply of liquid may last much longer.

The scientists working with the presently available implantable pumps are limited to those experiments which require that the liquid be pumped at a regular rate and for a relatively short amount of time. They could extend their investigations if they had available pumps which would (a) pump liquid into the subject's body over a longer period of time; (b) pump the liquid at exactly the desired times, i.e., repeated ejections of the liquid are obtained only at the desired moments; (c) pump the liquid in an exact and pre-defined quantity at each pump operation.

In the presently known implantable pumps it is not possible to increase the duration of the pump life by increasing the size of the pump, since it is desirable that the pump which is implanted within the laboratory animal be sufficiently small so as not to interfere with the normal health of the animal. If the pump were made larger, the effect of the experiment would become uncertain since the implantation of the pump itself may injure the animal.

In addition to the implantable pump, it is also possible to introduce drugs into a subject's bloodstream, or other fluids, by implanting slow-release materials such as drug pellets. One type of drug pellet contains micro-capsules which dissolve at different rates and release the drug over a selected time period. However, in drug pellets the rate of release is generally relatively rapid—a matter of days—and once the pellet has been implanted the rate of release is not controllable. The release rate may depend upon blood circulation and may vary, depending upon the individual subject. Such a varying and unknown rate is generally undesirable in an experimental situation. In addition, the release may be blocked by the body defense means, such as tissue growth. Such slow-release materials often fail to be available at the desired body location and at the desired concentration.

It will be understod that, although the discussion herein is in terms of "laboratory animal" or "subject", the invention is applicable to wherever a small externally activated pump may be utilized. For example, such a pump may, in the future, be approved for surgical implantation in humans as a means of ejecting a measured amount of drugs into the bloodstream.

OBJECTIVES AND FEATURES OF THE INVENTION

It is an objective of the present invention to provide a pump which is of sufficiently small size so that it may be surgically implanted within a laboratory animal, or other subject, without adversely affecting the health of the subject or adversely afecting any experimental regime in which the subject is involved.

It is a further objective of the present invention that the pumping rate of the pump be under the control of the experimenter; and that it not be a regular or constant rate (unless the experimenter desires a regular pumping rate) and, if desired by the experimenter, that the duration of the pumping may be extended for a relatively long period.

It is a still further objective of the present invention that the implantable pump may be removed and, possibly after cleaning, may be re-used by filling its reservoir with a new supply of liquid.

It is a further objective of the present invention that the implantable pump not be adversely affected by drugs or other liquids which it may contain.

It is a still further objective of the present invention that the apparatus which is used to initiate the pumping action be external to the subject and that the pumping action does not occur without the use of the exterior apparatus and that the external apparatus may be controlled to operate either automatically or manually.

It is a feature of the present invention to provide a system for the controlled release of a liquid into a subject, such as a laboratory animal, in an experimental setting. The system includes a surigcally implantable pump comprising a case means to enclose the pump mechanism. Preferably the case means is capsule-shaped and openable. An orifice means (a tube) through the case means permits the liquid to be ejected. The liquid is held in a refillable and flexible reservoir means within the case means.

A piston means is used to compress the reservoir means and thereby eject the liquid. The piston means moves only when the pump is positioned in a magnetic field, and magnetic responsive means moves the piston.

It is another feature of the present invention that the magnetic responsive means includes a spring loading the piston means. The spring is compressed when the reservoir is full and provides the force to move the piston. The spring is released by a ratchet and pawl mechanism which normally holds the spring compressed. The pawl is magnetically responsive and is operated by the magnetic field to release the ratchet step-by-step. Preferably the piston means is a piston which slides within the case member and forms a wall of the reservoir means.

BRIEF DESCRIPTION OF THE DRAWINGS

Other objectives and features of the present invention will be apparent from the following detailed description which provides the inventor's best presently known mode of practicing the invention. The detailed description should be taken in conjunction with the accompanying drawings, in which.

DETAILED DESCRIPTION OF THE INVENTION

Figure 1:
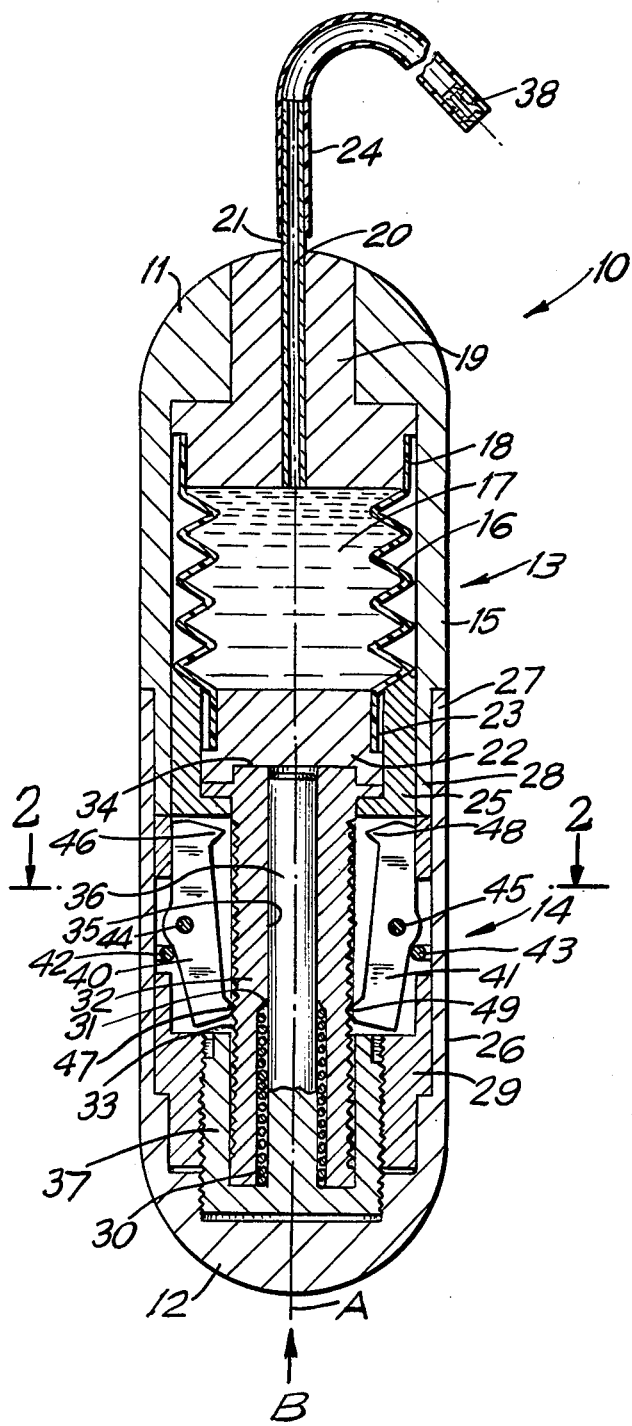
FIG. 1 is a cross-sectional view of the implantable pump of the present invention.

As shown in FIG. 1, the surgically implantable pump 10 of the present invention is generally shaped like a capsule. It is round in cross-section (perpendicular to the plane of FIG. 1) and its ends 11 and 12 are rounded. The pump 10 comprises two major portions, a reservoir portion 13 which contains the liquid to be pumped and a pump mechanism portion 14 which, under control of an external apparatus (described later) exerts pressure on the collapsible reservoir to force the liquid from the reservoir.

The liquid reservoir portion 13 includes a case member 15 which forms the top portion external wall of the pump 10. The case member 15, as the other portions of the pump which come into contact with the subject, is made of a non-magnetic responsive material which would not adversely react to the fluids of the subject's body. A number of plastic resins and metals have been approved for use in the body, for example, in connection with dental and surgical implantation.

The reservoir portion 13 includes a flexible and collapsible bellows 16, for example, of a plastic resin sheet material, positioned within the cavity formed by the case member 15. The reservoir bellows is hermetically sealed. The bellows 16 is a circle in cross-section and is pleated so that when pressure is exerted on its end it may be collapsed to a smaller volume. The bellows 16 contains the liquid 17 which is to be expelled into the subject, for example, into the bloodstream or the cerebrospinal fluid of the patient. The liquid may be a drug or an experimental liquid which is desired to be mixed in the body fluids of the subject.

The inner face of the top end 18 of the bellows 16 is adhered to the outer wall of the bushing 19, preferably of tissue compatible plastic resin. The bushing 19 has an inner bore 20 in which is secured the orifice tube 21. Although the embodiment shown in FIG. 1 shows the use of an orifice tube 21 to position the liquid more accurately, the use of such a tube is optional since the liquid may exit from the orifice formed by the top of the bore 20. The orifice tube 21 is continued by a catheter tube 24 having, at its outer end, a one-way valve 38.

A movable piston 22, of liquid-resistant plastic resin, is located at the opposite end of the bellows 16 and the inner wall of the lower end 23 of the bellows 16 is adhered to the outer side wall of the piston 22. The piston 22 is movable along the axis A, which is the imaginary central axis of the pump 10. The piston 22 is a disc-like member whose outer walls slidably fit within the piston support ring 25. The piston support ring 25 is secured to the case member 15 and has two opposed openings for the pawls and an integral bottom portion 25A.

The pump mechanism portion 14 includes a case member 26 which at its upper end 27 overlaps and is secured to the bottom end 28 of the case member 15. The case member 26 is of a material which has a low relative magnetic permeability. Preferably, the casing 26 is of a tissue compatible plastic resin which is compatible with the fluids of the animal in which it is implanted. The case member 26 at its bottom end (the end 12 of the pump) contains a first positioning ring 29 which is a tubular member.

The pump mechanism relies for its pumping action primarily upon a coil spring 30 of bronze or spring steel, which is compressed when the reservoir is filled with liquid. The coil spring 30 acts against the shoulder 31 of the ratchet member 32 having exterior ratchet teeth 33. The top face 34 of the ratchet member 32 is in contact with the bottom face of the piston 22. The ratchet member 32 has an inner bore 35. A post 36 is positioned within the bore 35 so that the ratchet member 32 may slide axially along post 36 in the direction of axis A and guided by the post 36. The post 36 is a portion of the bottom portion 25a which is fixed relative to the ring 29. The ring 29 is of soft magnetic material such as iron (high permeability, ferromagnetic, small coercive force, small remanence). The ratchet member, and the other metal members of the pump except for the pawls, are of non-magnetic materials such as copper, or brass or they may be of a plastic resin material.

Two spring-loaded pawls cooperate with the ratchet member 32. When the pawls are operated they permit upward motion of the ratchet member 32 in the direction of arrow B in a step-by-step manner. Although the pawl mechanism is shown as utilizing two opposed pawls each of which has teeth at either end and a centrally pivoted member, it will be understood that other types of pawl mechanisms may be used. For example, only one centrally pivoted pawl having an end pivot may be used. The two pawls 40 and 41 are similar in construction and each is loaded by a spring 42 which normally tends to force the pawl towards the central axis A. The pawls 40 and 41 are pivotable about the pivots, respectively 44,45, and each has at its ends two opposite teeth which are teeth 46,47 of the pawl 42 and the teeth 48,49 of the pawl 41. The pawls 40,41 have high relative magnetic permeability and they are ferromagnetic, of a soft magnetic material which material has a small coercive force, small remanence, low retentivity. The pawls are responsive to a magnetic field. The pawls, in a magnetic field, tend to swing so as to be aligned with the field. Preferably the pawls are of a soft magnetic material, such as soft iron, which is easily magnetized and demagnetized. The upper outer ends of the pawls are limited in their swinging motion by plastic resin ring 50.

Figure 2:
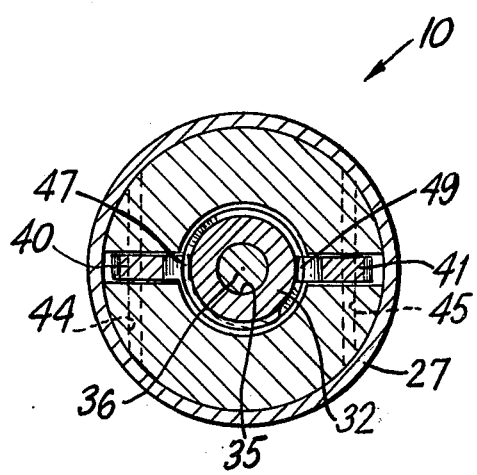
FIG. 2 is a cross-sectional view taken along line 2—2 of FIG. 1.
Figure 3:
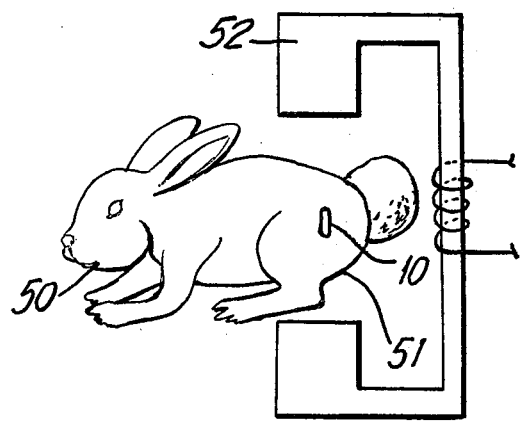
FIG. 3 is a perspective view illustrating a laboratory animal which is positioned within the range of the external apparatus which initiates the pumping action of the pump illustrated in FIG. 1.

In operation, as shown in FIG. 2, the pump 10 of the present invention is implanted in a laboratory animal 50 and a magnetic field is caused across the animal. The magnetic field may be created by a permanent magnet or by an electromagnet. Preferably an electromagnet is used to precisely control the duration of the magnetic field. The magnets preferably create a large flux of magnetic induction (B from 0.1 to 10 weber/meter$^2$, i.e. $10^3$ to $10^5$ gauss) in its air gap. When the magnetic field is caused near to the implanted pump, it acts to pivot the pawls 40 and 41 against the force of their spring 42. The magnetic field will cause the teeth 47 and 49 to move outwardly, i.e., away from the axis A, and cause the teeth 46 and 48 to move inwardly towards the axis A. The minimum duration of the magnetic field must be sufficiently long to move the teeth 47,49 outwardly, and teeth 46,48 inwardly. The magnetic field must cease (maximum duration) by the moment that the teeth 46,48 reach the ratchet member 32. If the magnetic field past that moment, it would pull teeth 46,48 outwardly and permit an additional release motion of the ratchet member 32. But because the magnetic field has ceased before the teeth 46,48 reach the ratchet member, a new and stable locked position is obtained with the teeth 48,48 locking the ratchet member 32. For example, the maximum duration of the magnetic field may be in the range 0.05 to 0.5 second. The pivoting motion of the pawls will permit the ratchet member 32 to move upwardly (in the direction of arrow B) one step, i.e., one tooth width. The upward motion of the ratchet member 32 will force the piston 22 upwardly (in the direction of arrow B) the distance between two teeth on the ratchet. Such upward motion of the piston 22 will slightly collapse the bellows 16 and eject the liquid 17 within the reservoir means out through the tube 21 and through the one-way valve 38. The amount of liquid expelled would be determined by the amount displaced by the piston movement and depends upon the relative size of the reservoir, the size of the piston and the spacing between the teeth on the ratchet member. These may be adjusted, for example, by utilizing different ratchet members having different teeth spacing, so as to provide the desired quantity of liquid to be expelled for each movement of the ratchet member.

The laboratory animal 50 is then removed from the magnetic field 51 of the electromagnet 52. If desired, the animal may be left in the range of the electromagnet and it is switched on and off either manually or automatically. No further pumping action of the liquid will occur while the animal is outside of the magnetic field. When it is desired that an additional ejection of liquid should occur, the laboratory animal 50 is again brought within the electromagnet, the electromagnet is switched on for a short period, for example, 0.05 to 0.5 second, causing the magnetic field, which again causes the pawls to pivot, releasing the ratchet member.

The force which ejects the liquid is from the compressed coil spring 30 and the magnetic field is used only as a trigger to control the release of the coil spring. Consequently, the magnetic field need not be strong since it does not directly expel the liquid.

Preferably the magnetic field is created by an electromagnet. An electromagnet has the advatages as to control and adjustment that (i) its magnetic flux may be determined by the voltage, (ii) the direction of the magnetic field may be exactly controlled by switching on and off of the electric current, (iii) the number of magnetic impulses may be controlled by the number of electrical impulses, and (iv) the intervals between impulses of current may be controlled. A limitation exists as to the minimum period between impulses due to the recovery time caused by the elasticity of the bellows, catheter, etc.

The relationship between the pump and the magnetic field may vary depending upon the desired positioning of the animal. It is preferred that the imaginary central axis of the pump be aligned with the direction of the magnetic flux (direction of magnetic lines of force). For example, if an electromagnet has a coil (solenoid type) the animal may be within the coil (internal field) or outside (external field) with the central pump axis parallel to the central axis of the coil.

The present invention has been described in terms of an embodiment of a pump which releases liquid, under control, a number of times. However, the pump may also be used for a single release of fluid. Fur such single release operation the pump mechanism may be simplified to having a single ratchet tooth on a spring-loaded ratchet which is released by a pawl. The pawl, of soft magnetic material, as in the prior described embodiment, is pulled from the ratchet tooth by a magnetic flux.

The casing of the pump is made in two parts, so that the case members may be separated for access to the internal mechanism, for example, for cleaning or repair. The pump may be refilled by moving the catheter tube 24 from the orifice tube 21 and forcing liquid into the reservoir. During refilling, if desired, the ratchet member may be displaced by utilizing a stiff wire which is inserted through the orifice tube 21 to act on the top face of the piston member 22 and depress the ratchet member, thereby compressing the coil spring 30. By proper selection of the angle of the teeth on the ratchet member and pawl, it is possible that the forced depression of the ratchet member 32 may cause the swinging of the pawls as the ratchet is depressed without catching the pawl teeth in the ratchet to prevent such forced depression of the ratchet member. Alternatively, the liquid may be injected into the reservoir under sufficient pressure so that the piston 22 is forced downwardly, thereby depressing the ratchet member 32 and compressing the coil spring 30. As another alternative, the case may be pulled part, by separating case parts 15,16, the ratchet depressed and the bellows filled by placing the catheter tube in the liquid and expanding the bellows to suck up the liquid.

What is claimed is:

1. A surgically implantable pump to eject liquid into a subject in which the pump is implanted, comprising a case means to enclose the pump, an orifice means through the case means by which liquid may be ejected from within the case means, a flexible reservoir means within the case means to hold the liquid and to eject it through the orifice means upon being compressed;

a piston means to compress the reservoir means; and
magnetic responsive means to move said piston means only when the pump is positioned in a magnetic field, so that liquid is ejected upon positioning the pump in the magnetic field, the said magnetic responsive means including a spring which loads the piston means and which is compressed when the reservoir is full and a ratchet and pawl mechanism holding the spring against release, the pawl being magnetically responsive, wherein the pawl releases the ratchet step-by-step each time it is positioned within the magnetic field.

2. A surgically implantable pump as in claim 1 wherein the collapsible reservoir means includes a bellows having foldable pleats.

3. A surgically implantable pump as the claim 1 wherein the piston means is a piston which slides within said case member and forms a wall of said reservoir means.

4. A surgically im:plantable pump as in claim 1 wherein said orifice means includes a one-way valve which permits ejection of the liquid without permitting fluid around the orifice means into the case means.

5. A surgically implantable pump to eject liquid into a subject in which the pump is implanted, comprising a case means to enclose the pump, an orifice means through the case means by which liquid may be ejected from within the case means, a flexible reservoir means within the case means to hold the liquid and to eject it through the orifice means upon being compressed;
 a piston means to compress the reservoir means;
 magnetic responsive means to move said piston means only when the pump is positioned in a magnetic field, so that liquid is ejected upon positioning the pump in the magnetic field; said magnetic responsive means including a pawl of magnetic responsive material pivotally mounted on the case means, a ratchet member acting on the piston means and releasable step-by-step by the motion of the pawl, and a coil spring acting on the ratchet and compressed upon filling the reservoir means, the coil spring being gradually uncompressed by movement of the ratchet.

6. A system for the controlled release of a liquid into a subject, including a surgically implantable pump comprising a case means to enclose the pump mechanism, an orifice means through the case means by which liquid may be ejected from within the case means, a flexible reservoir means within the case means to hold the liquid and to eject it through the orifice means upon being compressed;
 a piston means to compress the reservoir means;
 magnetic responsive means to move said piston means only when the pump is positioned in a magnetic field; said magnetic responsive means including a spring which loads the piston means and which is compressed when the reservoir is full and a ratchet and pawl mechanism holding the spring against release, the pawl being magnetically responsive, wherein the pawl each time it is positioned in the magnetic field releases the ratchet step-by-step; and
 magnetic field means to create a magnetic field within which the implanted pump may be positioned to thereby pump the liquid.

7. A system as in claim 6 wherein the piston means is a piston which slides within said case member and forms a wall of said reservoir means.

8. A system as in claim 6 wherein said orifice means includes a one-way valve which permits ejection of the liquid without permitting fluid around the orifice means into the case means.

9. A system as in claim 6 wherein the magnetic field means includes an electromagnet to create the magnetic field.

10. A system for the controlled release of a liquid into a subject, including a surgically implantable pump comprising a case means to enclose the pump mechanism, an orifice means through the case means by which liquid may be ejected from within the case means, a flexible reservoir means within the case means to hold the liquid and to eject it through the orifice means upon being compressed;
 a piston means to compress the reservoir means;
 magnetic responsive means to move said piston means only when the pump is positioned in a magnetic field, the said magnetic responsive means including a pawl of magnetic responsive material pivotally mounted on the case means, a ratchet member acting on the piston means and releasable step-by-step by the motion of the pawl, and a coil spring acting on the ratchet and compressed upon filling the reservoir means, the coil spring gradually being uncompressed by movement of the ratchet; and
 magnetic field means to create a magnetic field within which the implanted pump may be positioned to thereby pump the liquid.

* * * * *